United States Patent [19]
Putteman et al.

[11] Patent Number: 5,814,330
[45] Date of Patent: Sep. 29, 1998

[54] MUCOADHESIVE EMULSIONS CONTAINING CYCLODEXTRIN

[75] Inventors: Peter Putteman, Schellebelle; Marc Karel Jozef François, Kalmthout; Eric Carolus Leonarda Snoeckx, Beerse, all of Belgium

[73] Assignee: Janssen Pharmaceutica, N.V., Beerse, Belgium

[21] Appl. No.: 732,262

[22] PCT Filed: May 10, 1995

[86] PCT No.: PCT/EP95/01760

§ 371 Date: Oct. 31, 1996

§ 102(e) Date: Oct. 31, 1996

[87] PCT Pub. No.: WO95/31178

PCT Pub. Date: Nov. 23, 1995

[30] Foreign Application Priority Data

May 18, 1994 [EP] European Pat. Off. .............. 94201402

[51] Int. Cl.$^6$ ...................................... A61F 13/00
[52] U.S. Cl. .......................... 424/434; 424/435; 424/443; 424/430; 514/772.3
[58] Field of Search ...................................... 424/434, 435, 424/443, 430; 514/772.6, 772.2, 772.3

[56] References Cited

U.S. PATENT DOCUMENTS

| | | | |
|---|---|---|---|
| 5,055,303 | 10/1991 | Riley, Jr. | 424/436 |
| 5,324,718 | 6/1994 | Loftsson | 514/58 |
| 5,472,704 | 12/1995 | Santus | 424/435 |

FOREIGN PATENT DOCUMENTS

| | | |
|---|---|---|
| 2149362 | 11/1995 | Canada . |
| A-0197571 | 10/1986 | European Pat. Off. . |
| A-0335545 | 10/1989 | European Pat. Off. . |
| A-0579435 | 1/1994 | European Pat. Off. . |
| A-9315719 | 8/1993 | WIPO . |

*Primary Examiner*—Thurman K. Page
*Assistant Examiner*—D. Faulkner
*Attorney, Agent, or Firm*—Ellen Ciambrone Coletti

[57] ABSTRACT

The present invention relates to the use of a cyclodextrin or a derivative thereof as a mucoadhesive in an emulsion or aqueous solution, said cyclodextrin or derivative thereof being used in an amount from 10% to 70% by weight based on the total weight of the composition.

10 Claims, No Drawings

MUCOADHESIVE EMULSIONS CONTAINING CYCLODEXTRIN

CROSS REFERENCE TO RELATED APPLICATIONS

This application is based upon PCT Application Ser. No. PCT/EP 95/01760, filed May 10, 1995, which claims priority from European Patent Application Ser. No. 94.201.402.8, filed on May 18, 1994.

The development of an efficacious and readily manageable composition for vaginal use requires a satisfactory adhesion of the composition to the mucous membranes of the vagina in order to prevent the excretion of the product. A vaginal composition, therefore, should preferably show adequate mucoadhesive properties. The gels, foams, creams, suppositories and tablets that are presently used in the treatment of vaginal afflictions break down very rapidly after insertion into the vaginal cavity and have insufficient bioadherence to the vaginal walls. Hence, an unpleasant leakage is often experienced after administration and the effectivity of these products is limited. The present invention solves the problem by furnishing a mucoadhesive emulsion which comprises between 10% and 70% by weight of a cyclodextrin.

In particular, the present invention is concerned with the use of a cyclodextrin or a derivative thereof as a mucoadhesive in an emulsion or aqueous solution, said cyclodextrin or derivative thereof being used in an amount from 10% to 70% by weight based on the total weight of the composition. The subject mucoadhesive compositions may be applied to the mucous membranes of, for example, the nose, mouth and in particular of the vagina. Preferably, the composition comprises a drug such as, for example, an antibacterial, an antiviral, an anticonceptive or, in particular, an antifungal. Antifungals that may be included in the subject compositions are, for example, miconazole, clotrimazole, ketoconazole, terconazole, econazole, butoconazole, fluconazole, and, preferably, itraconazole.

A further aspect of the invention relates to mucoadhesive emulsions comprising itraconazole and a cyclodextrin or a derivative thereof in an amount between 10% and 70% by weight based on the total weight of the composition. Optionally, the subject compositions may comprise, apart from the cyclodextrin, further constituents having mucoadhesive properties.

Itraconazole is a broadspectrum antifungal compound and is disclosed in U.S. Pat. No. 4,267,179. In addition to their favourable mucoadhesive properties, the itraconazole compositions of the present invention show a further advantage in that cure rates in vaginal afflictions are higher and relapse rates are lower when compared to commercially available, antifungal compositions. Moreover, the present itraconazole compositions have an excellent physicochemical stability.

Itraconazole is the generic name of 4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4dihydro-2-(1-methylpropyl)-3H-1,2,4-triazol-3-one. The term "itraconazole" as used herein comprises the free base form, the pharmaceutically acceptable addition salts, the stereochemically isomeric forms thereof and the tautomeric forms thereof. The preferred itraconazole compound is the (±)-(cis) form of the free base form.

The acid addition forms may be obtained by reaction of the base form with an appropriate acid. Appropriate acids comprise, for example, inorganic acids such as hydrohalic acids, e.g. hydrochloric or hydrobromic acid; sulfuric acid; nitric acid; phosphoric acid and the like; or organic acids such as, for example, acetic, propanoic, hydroxyacetic, 2-hydroxypropanoic, 2-oxopropanoic, ethanedioic, propanedioic, butanedioic, (Z)-butenedioic, (E)-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. The term addition salt as used hereinabove also comprises the solvates. Said solvates are meant to be included within the scope of the present invention. Examples of such solvates are, e.g. the hydrates, alcoholates and the like.

The formation of an addition salt of the drug may be adopted to increase the solubility thereof in the aqueous phase.

The present compositions comprise a cyclodextrin or a derivative thereof. Appropriate cyclodextrin derivatives are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkyl-carbonyl, particularly acetyl; $C_{1-6}$alkyloxycarbonyl$C_{1-6}$alkyl or carboxy$C_{1-6}$alkyl-oxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD.

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The M.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. In the cyclodextrin hydroxyalkyl derivatives for use in the compositions according to the present invention the M.S. as determined by mass spectrometry is in the range of 0.125 to 10, in particular of 0.3 to 3, or from 0.3 to 1.5. Preferably the M.S. ranges from about 0.3 to about 0.8, in particular from about 0.35 to about 0.5 and most particularly is about 0.4. M.S. values determined by NMR or IR preferably range from 0.3 to 1, in particular from 0.55 to 0.75.

The average substitution degree (D.S.) refers to the average number of substituted hydroxyls per anhydroglucose unit. The D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. In the cyclodextrin derivatives for use in the compositions according to the present invention the D.S. as determined by MS is in the range of 0.125 to 3, in particular of 0.2 to 2 or from 0.2 to 1.5. Preferably the D.S. ranges from about 0.2 to about 0.7, in particular from about 0.35 to about 0.5 and most particularly is about 0.4. D.S. values determined by NMR or IR preferably range from 0.3 to 1, in particular from 0.55 to 0.75.

Preferably the amount of unsubstituted β- or γ-cyclodextrin is less than 5% of the total cyclodextrin content and in particular is less than 1.5% Particularly interesting cyclodextrin derivative is randomly methylated β-cyclodextrin. More particular β- and γ-cyclodextrin hydroxyalkyl derivatives for use in the compositions according to the present invention are partially substituted cyclodextrin derivatives wherein the average degree of alkylation at hydroxyl groups of different positions of the anhydroglucose units is about 0% to 20% for the 3 position, 2% to 70% for the 2 position and about 5% to 90% for the 6 position.

Most preferred cyclodextrin derivatives for use in the present invention are those partially substituted β-cyclodextrin ethers or mixed ethers having hydroxypropyl, hydroxyethyl and in particular 2-hydroxypropyl and/or 2-(1-hydroxypropyl) substituents. The most preferred cyclodextrin derivative for use in the compositions of the present invention is hydroxypropyl-β-cyclodextrin having a M.S. in the range of from 0.35 to 0.50 and containing less than 1.5% unsubstituted β-cyclodextrin. M.S. values determined by NMR or IR preferably range from 0.55 to 0.75.

Substituted cyclodextrins can be prepared according to procedures described in U.S. Pat. No. 3,459,731, EP-A-0,149,197, EP-A-0,197,571, U.S. Pat. No. 4,535,152, WO-90/12035 and GB-2,189,245. Other references describing cyclodextrins for use in the compositions according to the present invention, and which provide a guide for the preparation, purification and analysis of cyclodextrins include the following: "Cyclodextrin Technology" by J ózsef Szejtli, Kluwer Academic Publishers (1988) in the chapter Cyclodextrins in Pharmaceuticals; "Cyclodextrin Chemistry" by M. L. Bender et al., Springer-Verlag, Berlin (1978); "Advances in Carbohydrate Chemistry", Vol. 12 Ed. by M. L. Wolfrom, Academic Press, New York (157) in the chapter The Schardinger Dextrins by Dexter French at p. 189–260; "Cyclodextrins and their Inclusions Complexes" by J. Szejtli, Akademiai Kiado, Budapest, Hungary (1982); I. Tabushi in Acc. Chem. Research, 1982, 15, p. 66–72; W. Sanger, Angewandte Chemie, 92, p. 343–361 (1981); A. P. Croft and R. A. Bartsch in Tetrahedron, 39, p. 1417–1474 (1983); Irie et al. Pharmaceutical Research, 5, p. 713–716, (1988); Pitha et al. Int. J. Pharm. 29, 73, (1986); DE 3,118,218; DE-3,317,064; EP-A-94,157; U.S. Pat. No. 4,659,696; and U.S. Pat. No. 4,383,992.

Cyclodextrin and the derivatives thereof are known as solubility and/or stability enhancing agents. In particular for the itraconazole compositions of the present invention, the cyclodextrin has a favourable effect on the solubility of the antifungal in the aqueous phase of the composition. Unexpectedly, compositions comprising more than 10% by weight based on the total weight of the formulation of a cyclodextrin or a derivative thereof were found to exhibit useful mucoadhesive properties.

Hereinafter, the amounts of each of the ingredients in the emulsions are expressed as percentages by weight based on the total weight of the formulation. Similarly, ratios are intended to define weight-by-weight ratios.

In particular, the concentration of the drug may range from 0.1% to 20%, preferably from 0.5% to 10%, more preferably from 1% to 5% and in particular is 1% to 2%. The amount of cyclodextrin in the present compositions ranges from 10% to about 70%, preferably from 25% to 60% and in particular is 40% to 50%. Generally, the ratio of the drug, in particular itraconazole, to the cyclodextrin ranges from about 1:700 to 1:2, preferably from 7:120 to 1:10 and in particular is between 1:50 and 1:25.

The emulsions of the present invention consist of an aqueous phase and an oil phase. The compositions may take the form of an oil-in-water (O/W) emulsion, in which the oil phase is considered to be the internal or dispersed phase while the aqueous phase is considered the external or continuous phase. The subject O/W emulsions have the advantage that the drug, in particular itraconazole, is dissolved in the aqueous, hence external, phase, which is in direct contact with the mucous membranes. The latter will enhance the effectivity of the drug and may lower the required number of applications per time unit.

Alternatively, the compositions may take the form of a water-in-oil (W/O) emulsion in which the aqueous phase is considered to be the internal or dispersed phase while the oil phase is considered the external or continuous phase. The W/O emulsion has the advantage that it shows favourable spreading properties and optimal mucoadhesive properties, thus constituting a particularly user-friendly embodiment of the invention. Preferably, the oil phase of the emulsion comprises a mineral oil and more in particular comprises paraffin oil.

The compositions may be applied in the form of conventional products such as creams, capsules, pessaries, gelatin capsules, coated tampons, preparations for the direct introduction in the vagina by means of cannula supplying devices with manual or mechanic pressure (spray foam) and the like.

In addition to the drug and the cyclodextrin constituents, the subject compositions may further comprise various additives such as emulsifiers, buffer systems, acids or bases, stabilizing agents, thickening agents, preservatives and the like.

Suitable emulsifiers are, for example, anionic, cationic or, more preferably, nonionic emulsifiers, such as, for example, sucrose esters; glucose esters; polyoxyethylated fatty esters; polyoxyethylated fatty alcohol ethers; glycerol esters, e.g. glycerol monostearate; sorbitan esters, e.g. sorbitan monopalmitate (=Span 40®), sorbitan monostearate (=Span 60®); polyoxyethylene derivatives of sorbitan esters, e.g. polysorbate 40 (=Tween 40®), polysorbate 60 (=Tween 60®), cetyl dimethicon copolyol and the like. Preferably cetyl dimethicon copolyol is used in an amount of 0.5 to 10%, preferably in an amount of approximately 2%.

Buffer systems comprise mixtures of appropriate amounts of an acid such as phosphoric, succinic, tartaric, lactic, or citric acid, and a base, in particular sodium hydroxide or disodium hydrogen phosphate. Preferably, said buffer systems maintain the pH of the formulation between 1 and 4, more preferably between 2 and 3. Alternatively, the pH of the composition can be fixed upon addition of an acid such as hydrochloric acid or a base such as sodium hydroxide and the like. The composition of the present invention having a pH below 3 were well tolerated by the mucous membranes of the vagina. This is clearly unexpected in view of the pH of the art vaginal compositions which are usually only slightly acid (pH of about 4). Further, the low pH of the composition will have a beneficial influence on the antimicrobial effect of the composition.

Suitable stabilizing agents which ensure the physicochemical stability of the composition are for example inorganic salts, e.g. sodium chloride and the like, 1,2-propanediol, glycerin, and the like. Preferably, sodium chloride and 1,2-propanediol are used in an amount of 0.5 to 5% each, preferably in an amount of approximately 1% sodium chloride and 3% 1,2-propanediol.

The viscosity of the subject formulations may be increased upon the addition of thickening agents, such as, for example lyophobic agents such as, for example, 1-octadecanol, 1-hexadecanol, glycerol monostearate, Carnuba wax, beeswax, trihydroxystearate and the like; or lyophilic agents such as, for example, cellulose derivatives, e.g. sodium carboxymethylcellulose; polyethylene glycol; chitin and the derivatives thereof, e.g. chitosan; poloxamers; clays; natural gums; starch derivatives; and the like. Preferably trihydroxystearate is used in an amount of 0.05 to 5%, preferably in an amount of approximately 0.5%.

Preferred compositions are those wherein:
the amount of itraconazole is 0.1 to 5%;
the amount of cyclodextrin is 10 to 70%;
the amount of thickening agent is 0.05 to 5%;
the amount of emulsifier is 0.5 to 10%; and
the amount of stabilizing agent is 0.5 to 10%.

More preferred compositions comprise by weight based on the total weight of the composition:
(a) 0.5 to 3% itraconazole;
(b) 30 to 70% cyclodextrin;
(c) 0.1 to 1% thickening agent;
(d) 1 to 5% emulsifier,
(e) 1 to 4% stabilizing agent;
(f) buffer, acid or base to maintain the pH of the composition between 1 and 3;
(g) 0.5 to 50% of a dermatologically acceptable oil; and
(h) water.

A particularly preferred composition comprises approximately by weight based on the total weight of the composition:
(a) 1% itraconazole;
(b) about 43% hydroxypropyl-β-cyclodextrin;
(c) 0.5% trihydroxystearate;
(d) 2% cetyl dimethicon copolyol;
(e) 1% sodium chloride and 3% 1,2-propanediol;
(f) about 0.4% hydrochloric acid and a sufficient amount of sodium hydroxide to maintain the pH of the composition at about pH=2.7;
(g) 20% paraffin oil; and
(h) water.

Another particularly preferred composition comprises approximately by weight based on the total weight of the composition:
(a) 2% itraconazole;
(b) about 50% hydroxypropyl-β-cyclodextrin;
(c) 0.5% trihydroxystearate;
(d) 2% cetyl dimethicon copolyol;
(e) 1% sodium chloride and 3% 1,2-propanediol;
(f) about 0.9% hydrochloric acid and a sufficient amount of sodium hydroxide to maintain the pH of the composition at about pH=2.2;
(g) 12.5% paraffin oil; and
(h) water.

To prepare the pharmaceutical compositions of this invention, an effective amount of the drug and the cyclodextrin is combined in intimate admixture with the water and oil phase of the emulsion. In a preferred mode, the preparation of the subject compositions comprises the following steps:

(1) The aqueous phase is prepared containing the drug and the cyclodextrin;
(2) The acid, base or buffer substances are added to phase (1) until the desired pH is reached;
(3) The oil phase is prepared upon stirring at a temperature between 80° and 85° C.,
(4) Phase (3) is cooled to below 40° C. and the emulsifiers are added;
(5) Phase (2) and phase (4) are mixed upon stirring.

Optionally, the thus obtained compositions may be homogenized using art-known procedures.

Optionally, the above procedure is conducted under an inert atmosphere, e.g. nitrogen or oxygen-free argon. It may be advantageous to use micronized forms of the drug. Micronized forms can be prepared by micronization techniques known in the art, e.g. by milling in appropriate mills and sieving through appropriate sieves.

In a further aspect, the present invention is concerned with the use of the compositions as defined hereinabove for preventing, reducing or curing afflictions of the mucous membranes, in particular of the vagina.

The present invention is also concerned with a method of preventing, reducing or curing disorders of the mucous membranes and afflictions related thereto, in particular infections of the vagina, in warm-blooded animals, in particular human beings, which comprises administering vaginally to said warm-blooded animals a composition as defined hereinabove, in an amount effective in preventing, reducing or curing the affliction.

In general it is contemplated that an effective dosage of the subject compositions would be a treatment of once daily for about 1 to 3 days. It is evident that said effective dosage may be lowered or increased depending on the response of the treated subject and/or depending on the evaluation of the physician prescribing the compositions of the instant invention. The effective dosage mentioned hereinabove is therefore a guideline only and is not intended to limit the scope or use of the invention to any extent.

The following examples are intended to illustrate the scope of the present invention in all its aspects and not to limit it thereto.

EXAMPLE 1

F1 (cream)

| Ingredient | Quantity, mg/g cream |
|---|---|
| itraconazole | 10 |
| hydrochloric acid p.a. | 4.4 |
| hydroxypropyl-β-CD | 436 |
| 1,2-propanediol | 30 |
| sodium hydroxide | q.s. pH = 2.7 |
| sodium chloride | 10 |
| paraffin oil | 200 |
| cetyl dimethicon copolyol | 20 |
| trihydroxystearate | 5 |
| purified water | q.s. ad 1 g |

Procedure:

(1) 10 mg itraconazole and 4.4 mg hydrochloric acid were dissolved in 30 mg 1,2-propanediol upon stirring at 35°–40° C.;

(2) 436 mg hydroxypropyl-β-CD was dissolved in 284.6 mg purified water upon stirring;

(3) Then, phase (1) and phase (2) were mixed upon stirring;

(4) 10 mg of sodium chloride was dissolved in phase (3) upon stirring;

(5) Concentrated sodium hydroxide was added until pH=2.7;

(6) 200 mg paraffin oil and 5 mg trihydroxystearate were mixed upon stirring (25 rpm) at 80°–85° C. for 30 minutes;

(7) Phase (6) was cooled upon stirring to below 40° C. and 20 mg cetyl dimethicon copolyol was added upon stirring;

(8) Then, phase (5) and phase (7) were mixed upon stirring for 30 minutes.

In a similar way there were prepared:

F2 (cream)

| Ingredient | Quantity, mg/g cream |
| --- | --- |
| itraconazole | 20 |
| hydrochloric acid p.a. | 8.9 |
| hydroxypropyl-β-CD | 500 |
| 1,2-propanediol | 30 |
| sodium hydroxide | q.s. pH = 2.2 |
| sodium chloride | 10 |
| paraffin oil | 125 |
| cetyl dimethicon copolyol | 20 |
| trihydroxystearate | 5 |
| purified water | q.s. ad 1 g |

F3 (cream)

| Ingredient | Quantity, mg/g cream |
| --- | --- |
| itraconazole | 25 |
| hydrochloric acid p.a. | 11.1 |
| hydroxypropyl-β-CD | 530 |
| 1,2-propanediol | 35 |
| sodium hydroxide | q.s. pH = 2 |
| paraffin oil | 45 |
| cetyl dimethicon copolyol | 15 |
| trihydroxystearate | 5 |
| purified water | q.s. ad 1 g |

EXAMPLE 2

Six female New Zealand White rabbits were administered intravaginally 0.05 g of cream F3 per kg body weight. All animals were examined daily during 4 weeks for clinical signs of waning health, abnormal behaviour or unusual appearance, occurrence of untoward clinical effects and manifestations of irritant, toxic and pharmacological response.

Conclusions:

The cream under investigation did not produce an effect on clinical appearance and behaviour. No leakage out of the vagina was seen in any of the test animals during the 4 week period.

EXAMPLE 3

Test solution:

| | |
| --- | --- |
| benzoic acid | 2 mg |
| hydroxypropyl-β-CD | 250 mg |
| concentrated HCl | q.s. pH = 3.04 |
| purified water | q.s. ad 1 g |

Three female Albino rabbits were administered intravaginally 0.25 g of the test solution per kg body weight during 5 consecutive days. No expulsion of the formulation was seen in any of the test animals during the 5 day period.

We claim:

1. A mucoadhesive emulsion composition comprising a drug selected from the group consisting of antibacterial, antiviral, contraceptive, and antifungal agents, and a cyclodextrin or a derivative thereof in an amount from 10% to 70% by weight based on the total weight of the composition.

2. The composition of claim 1 wherein the drug is an antifungal agent.

3. The composition of claim 1 wherein the composition is a vaginal formulation.

4. A mucoadhesive emulsion composition comprising by weight based on the total weight of the composition 0.5 to 3% intraconazole;

30 to 70% cyclodextrin;

0.1 to 1% thickening agent;

1 to 5% emulsifier;

1 to 4% stabilizing agent;

buffer, acid or base to maintain the pH of the composition between 1 and 3;

0.5 to 50% of a dermatologically acceptable oil;

and water.

5. The mucoadhesive emulsion composition of claim 2 comprising itraconazole and a cyclodextrin or a derivative thereof in an amount of from 10% to 70% by weight based on the total weight of the composition.

6. A composition according to claim 5 wherein the emulsion is a water-in-oil emulsion.

7. A composition according to claim 5 wherein the pH is between 1 and 4.

8. A composition according to claim 5 wherein the weight-by-weight ratio of itraconazole to cyclodextrin ranges from 1:700 to 1:2.

9. A composition according to claim 5 wherein the amount of itraconazole is 0.1 to 5%;

the amount of cyclodextrin is 10 to 70%;

the amount of thickening agent is 0.05 to 5%;

the amount of emulsifier is 0.5 to 10%; and the amount of stabilizing agent is 0.5 to 10%.

10. The composition according to claim 9, wherein the cyclodextrin is hydroxypropyl-β-cyclodextrin.

* * * * *